US009498240B1

(12) United States Patent
Godley

(10) Patent No.: US 9,498,240 B1
(45) Date of Patent: Nov. 22, 2016

(54) DEVICE FOR CLEANING A TONGUE AND METHOD OF USE

(76) Inventor: Mark Robert Godley, Charlotte, NC (US)

(*) Notice: Subject to any disclaimer, the term of this patent is extended or adjusted under 35 U.S.C. 154(b) by 327 days.

(21) Appl. No.: 13/610,978

(22) Filed: Sep. 12, 2012

(51) Int. Cl.
*A61B 17/24* (2006.01)
*A61F 11/00* (2006.01)

(52) U.S. Cl.
CPC ............ *A61B 17/24* (2013.01); *A61B 17/244* (2013.01); *A61B 2017/246* (2013.01); *A61F 11/006* (2013.01)

(58) Field of Classification Search
CPC .................... A61B 17/244; A61F 11/006
See application file for complete search history.

(56) References Cited

U.S. PATENT DOCUMENTS

| | | | | |
|---|---|---|---|---|
| 2,491,274 A | * | 12/1949 | McNeill | 604/1 |
| 3,943,592 A | * | 3/1976 | Bhaskar et al. | 15/160 |
| D309,528 S | * | 7/1990 | Valenti | D4/104 |
| D332,352 S | * | 1/1993 | Caldwell et al. | D4/104 |
| D360,262 S | * | 7/1995 | Ly | D24/147 |
| 5,735,864 A | * | 4/1998 | Heisinger, Jr. | 606/161 |
| 5,766,248 A | * | 6/1998 | Donovan | 606/1 |
| 5,792,159 A | * | 8/1998 | Amin | 606/161 |
| 5,916,228 A | * | 6/1999 | Ripich et al. | 606/161 |
| D411,884 S | * | 7/1999 | Dewti | D24/146 |
| 5,938,673 A | * | 8/1999 | DePierro et al. | 606/161 |
| 5,944,519 A | * | 8/1999 | Griffiths | 433/80 |
| 6,010,268 A | * | 1/2000 | Sereg et al. | 401/207 |
| 6,032,315 A | * | 3/2000 | Liebel | 15/160 |
| 6,083,235 A | * | 7/2000 | Wagner | 606/161 |
| 6,116,252 A | * | 9/2000 | Stelmach | 132/309 |
| 6,132,445 A | * | 10/2000 | Pavanelli | 606/161 |
| 6,171,323 B1 | * | 1/2001 | Potti et al. | 606/161 |
| 6,286,173 B1 | * | 9/2001 | Briones | 15/167.1 |
| 6,352,545 B1 | * | 3/2002 | Wagner | 606/161 |
| 6,402,768 B1 | * | 6/2002 | Liebel | 606/161 |
| 6,625,839 B2 | * | 9/2003 | Fischer et al. | 15/160 |
| 6,721,987 B2 | * | 4/2004 | McDevitt et al. | 15/227 |
| 6,921,409 B2 | * | 7/2005 | Richard | 606/161 |
| 7,039,984 B1 | * | 5/2006 | Watanabe et al. | 15/167.1 |
| D523,299 S | * | 6/2006 | Johnson | D7/653 |
| 7,552,501 B2 | * | 6/2009 | Yang et al. | 15/227 |
| 7,674,058 B2 | * | 3/2010 | Berger Sharp et al. | 401/7 |
| 7,815,383 B2 | * | 10/2010 | Hall | 401/6 |
| 8,800,091 B2 | * | 8/2014 | Hohlbein | 15/111 |
| 8,806,695 B2 | * | 8/2014 | Moskovich et al. | 15/167.1 |
| 8,858,580 B2 | * | 10/2014 | Schaefer et al. | 606/161 |
| 2001/0041903 A1 | * | 11/2001 | Richard | 606/161 |

(Continued)

OTHER PUBLICATIONS

Lindermann, B 1999. Receptor seeks ligand: on the way to cloning the molecular receptors for sweet and bitter taste. Nat. Med. 5:381-382 doi:10.1038/7377.*

*Primary Examiner* — Gregory Anderson
*Assistant Examiner* — Son Dang
(74) *Attorney, Agent, or Firm* — Ted Masters

(57) ABSTRACT

A device for cleaning a tongue includes a body having a top surface, an opposite bottom surface, a proximal section, and a distal section. An upwardly projecting ridge is centrally disposed at the proximal section. The ridge has a first downwardly sloping side which is shaped and dimensioned to receive one of the two fingers, and a second downwardly sloping side which is shaped and dimensioned to receive the other of the two fingers. The bottom surface forms a cavity at the proximal section, the cavity is shaped and dimensioned to receive the thumb. A tongue-cleaning pad is disposed on the bottom surface at the distal section. The device can be held by either hand and used to clean the tongue.

20 Claims, 7 Drawing Sheets

(56) References Cited

U.S. PATENT DOCUMENTS

| | | | |
|---|---|---|---|
| 2002/0019645 A1* | 2/2002 | Fischer | A61B 17/244 606/161 |
| 2004/0200748 A1* | 10/2004 | Klassen et al. | 206/368 |
| 2007/0209133 A1* | 9/2007 | Linzell | 15/209.1 |
| 2007/0282360 A1* | 12/2007 | Smith et al. | 606/161 |
| 2008/0155773 A1* | 7/2008 | Chen | 15/143.1 |
| 2009/0130637 A1* | 5/2009 | Pantangco, III | 433/216 |
| 2009/0235474 A1* | 9/2009 | Seigel | 15/111 |
| 2013/0130196 A1* | 5/2013 | Joyashiki et al. | 433/87 |
| 2013/0233347 A1* | 9/2013 | Wang et al. | 134/6 |
| 2014/0014543 A1* | 1/2014 | Hohlbein | 206/368 |
| 2014/0130280 A1* | 5/2014 | Bouboushian | 15/227 |

\* cited by examiner

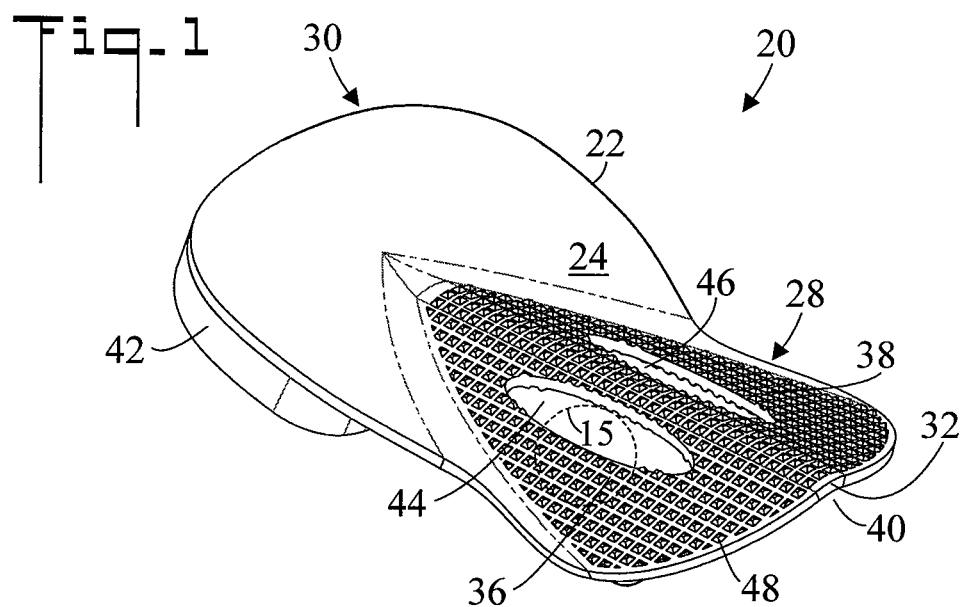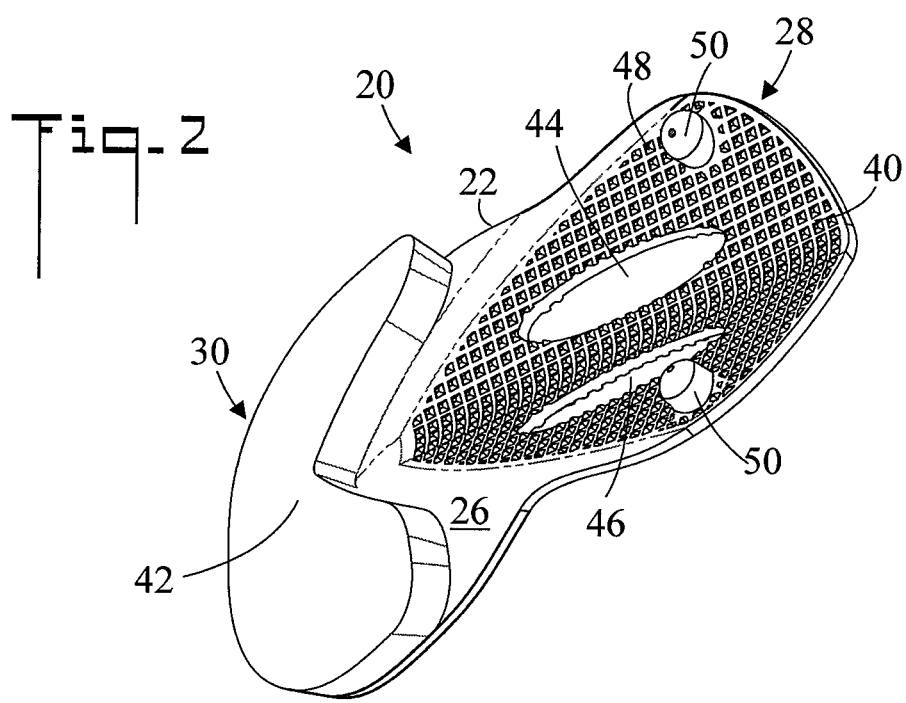

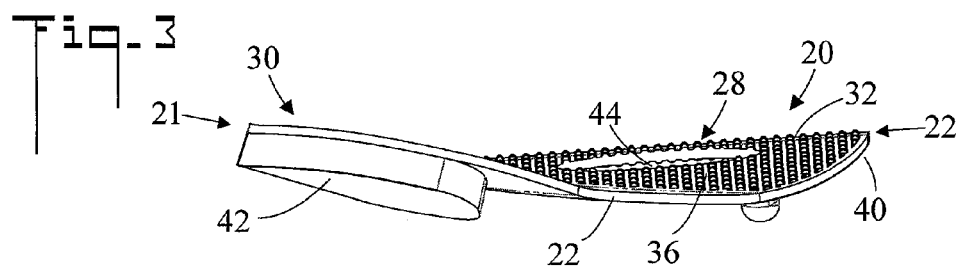
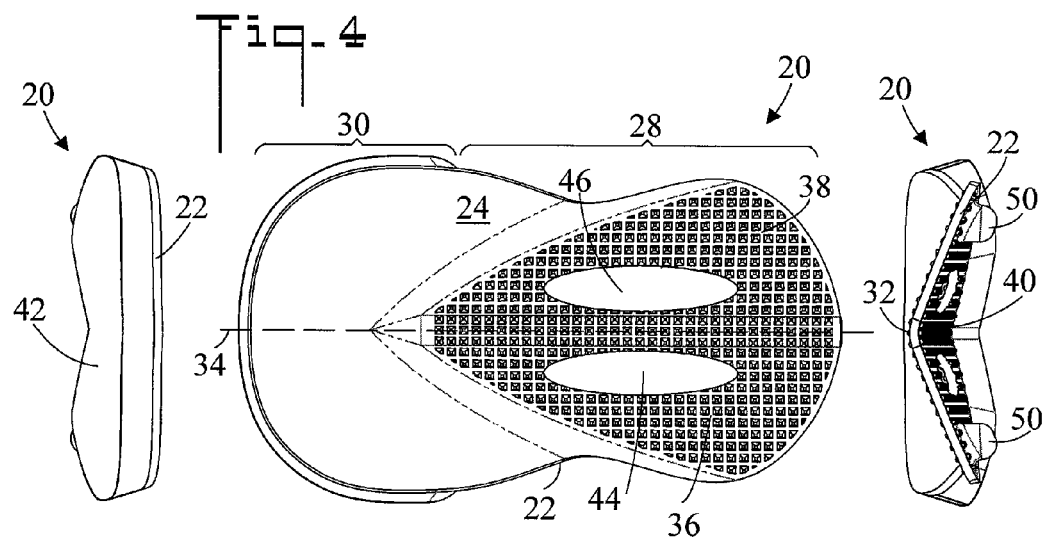
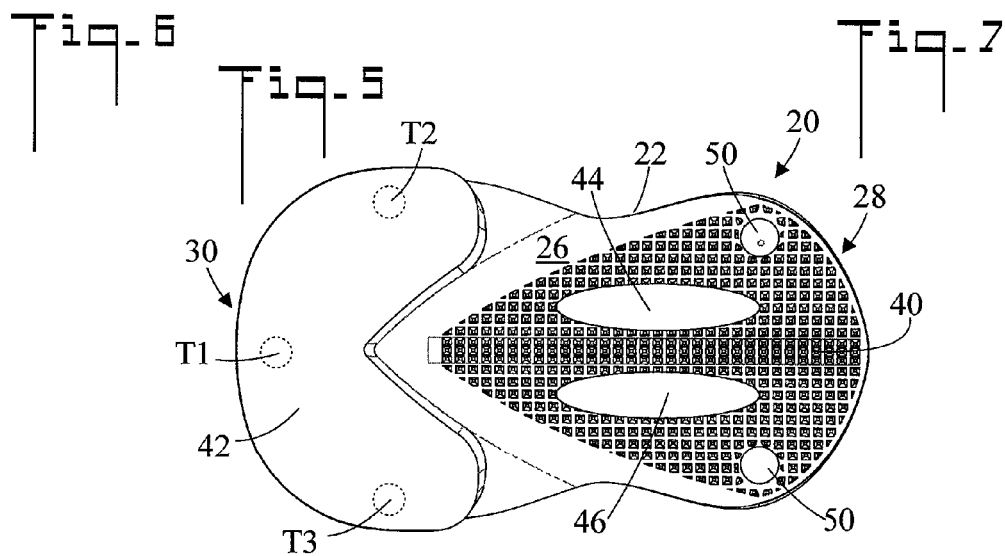

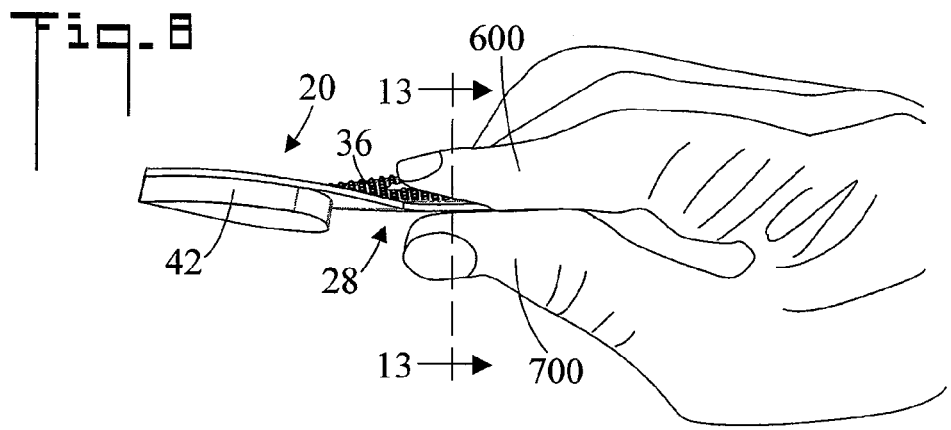
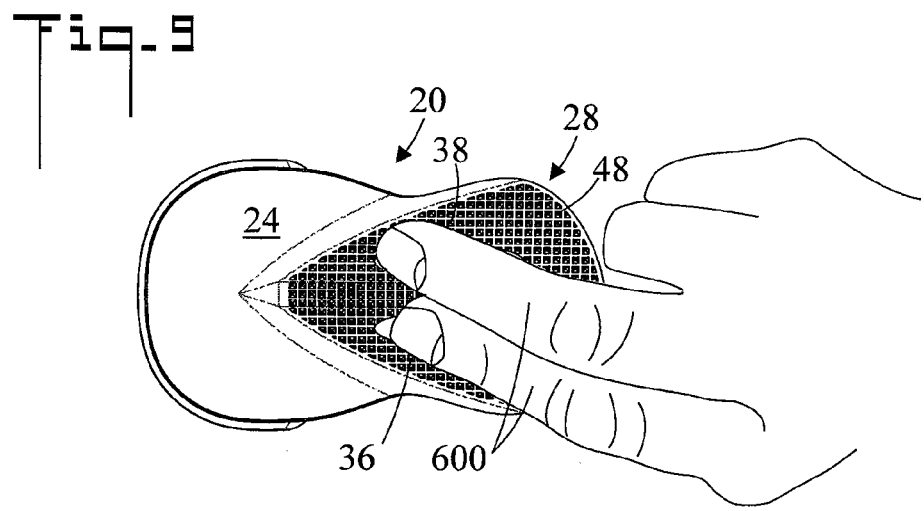
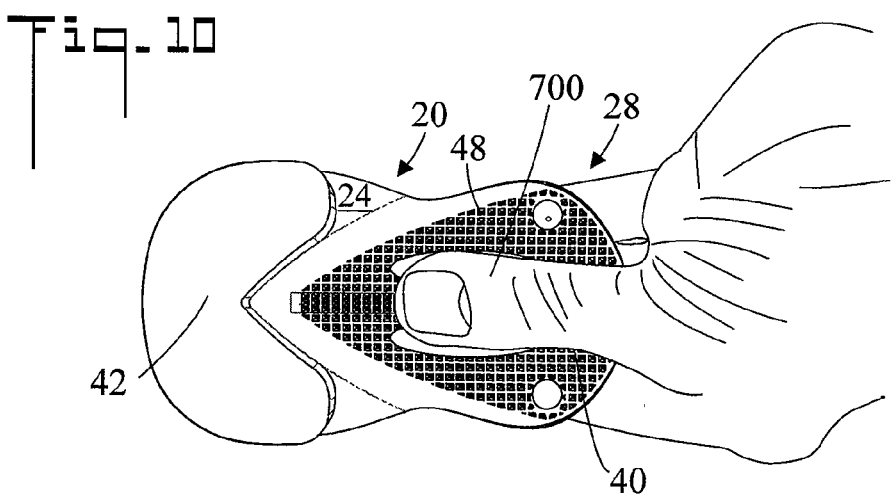

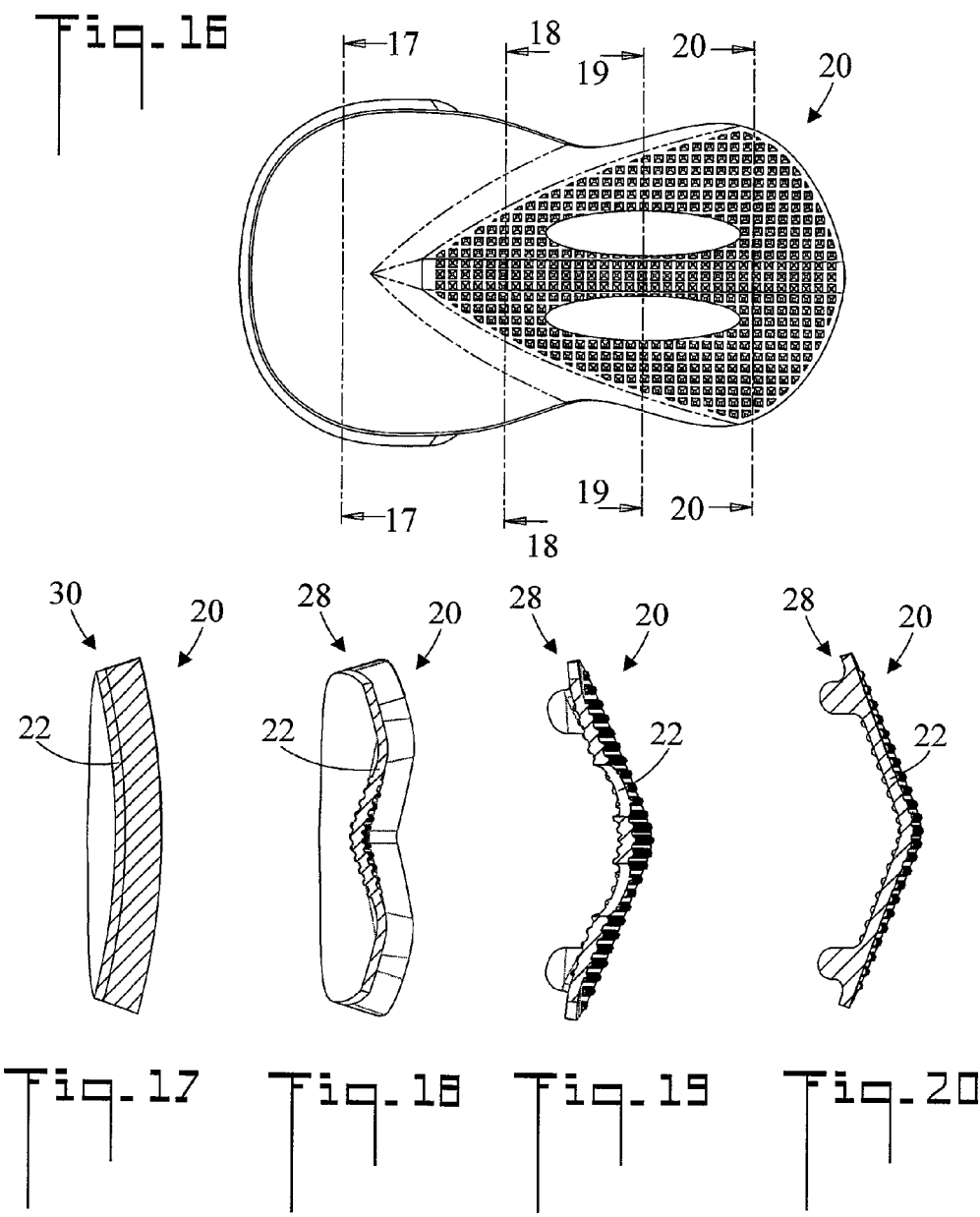

DEVICE FOR CLEANING A TONGUE AND METHOD OF USE

CROSS REFERENCE TO RELATED APPLICATION

None.

TECHNICAL FIELD

The present invention pertains generally to personal hygiene, and more particularly to a device for cleaning the tongue.

BACKGROUND OF THE INVENTION

When food or drink are consumed, a residue is left in the mouth. Because of its rough surface, the tongue is a particularly efficient collector of such residue. This residue can be a source of odor-causing bacteria, and as such, it is desirable to periodically clean the surface of the tongue.

BRIEF SUMMARY OF THE INVENTION

The present invention is directed to a device for cleaning the tongue. The device can be held in either hand by two fingers and the thumb. The shape of the device allows a tongue-cleaning pad to be pressed down on the tongue, thus allowing pressure combined with a forward and backward motion to clean, refresh and then collect residue from the surface of the tongue. The device wipes the tongue, rather than other devices which scrape the tongue, and as such collects debris, bacteria and film that traditional devices and methods miss. The device is disposable and only to be used once before discarding.

The device solves one problem of oral health by removing harmful debris, bacteria and plaque from the tongue. In one embodiment, the device is scented and/or flavored. The pad can have a light or florescent tint for observing or analyzing the residue the device has removed from the tongue. It also can lessen alcohol inebriation by reducing the alcohol that has collected on the tongue. The pad is s wide enough to clean the entire surface of the tongue in one pass.

In accordance with an embodiment, a device for cleaning a tongue is holdable by two fingers and a thumb of one hand. The device includes a body which has a top surface, an opposite bottom surface, a proximal section, and a distal section. An upwardly projecting ridge is centrally disposed at the proximal section. The ridge has a first downwardly sloping side which is shaped and dimensioned to receive one of the two fingers, and a second downwardly sloping side opposite the first downwardly sloping side which is shaped and dimensioned to receive the other of the two fingers. The bottom surface forms a cavity at the proximal section, the cavity is shaped and dimensioned to receive the thumb. A tongue-cleaning pad is disposed on the bottom surface at the distal section.

In accordance with another embodiment, a first aperture is disposed in the first downwardly sloping side, the aperture extending through the body from the top surface to the bottom surface. A second aperture is disposed in the second downwardly sloping side, the second aperture extending through the body from the top surface to the bottom surface. When the two fingers are placed on the first and second downwardly sloping sides and the thumb is placed in the cavity, the two fingers each touch the thumb.

In accordance with another embodiment, at the proximal section, the top and bottom surfaces are covered with a plurality of friction enhancing protuberances.

In accordance with another embodiment, two downwardly projecting legs are connected to the bottom surface at the proximal section.

In accordance with another embodiment, the proximal section is curved in a downward direction, and the distal section and the pad are curved in an upward direction.

In accordance with another embodiment, the pad is fabricated from a light colored absorbent material.

In accordance with another embodiment, the tongue has different areas which sense different tastes. A plurality of different tastes are disposed on the pad, the tastes being physically located on the pad so that when the pad touches the tongue, a taste on the pad abuts the area of the tongue which senses the taste.

Other embodiments, in addition to the embodiments enumerated above, will become apparent from the following detailed description, taken in conjunction with the accompanying drawings, which illustrate, by way of example, the principles of the device and method of use.

BRIEF DESCRIPTION OF THE DRAWINGS

FIG. 1 is a top perspective view of a device for cleaning a tongue;

FIG. 2 is a bottom perspective view of the device;

FIG. 3 is a side elevation view of the device;

FIG. 4 is a top plan view of the device;

FIG. 5 is a bottom plan view of the device;

FIG. 6 is an end view of the device;

FIG. 7 is an opposite end view of the device;

FIG. 8 is a reduced side elevation view of the device being held by a user;

FIG. 9 is a reduced top plan view of the device being held by the user;

FIG. 10 is a bottom plan view of the device being held by the user;

FIG. 16 is a top plan view of the device and cross sectional lines;

FIG. 17 is a cross sectional view along the line 17-17 of FIG. 16;

FIG. 18 is a cross sectional view along the line 18-18 of FIG. 16;

FIG. 19 is a cross sectional view along the line 19-19 of FIG. 16;

FIG. 20 is a cross sectional view along the line 20-20 of FIG. 16;

DETAILED DESCRIPTION OF THE INVENTION

Figure 11:
FIG. 11 is a reduced side elevation view of a user preparing to use the device.

Referring initially to FIGS. 1-7, there are illustrated top perspective, bottom perspective, side elevation, top plan, bottom plan, end, and opposite end views respectively of a device for cleaning a tongue 500 (refer to FIG. 12), the device generally designated as 20. Device 20 is holdable by two fingers 600 and a thumb 700 of one hand (refer to FIGS. 8-10). That is, device 20 can be gripped by either hand (right or left), using two of the four fingers 600 (e.g. index and middle) and the opposing thumb 700. Device 20 includes a body 22 having a top surface 24, an opposite bottom surface 26, a proximal section 28, and a distal section 30. When device 20 is used by a standing or seated user, top surface 24 generally faces up, and bottom surface 26 generally faces down (refer to FIGS. 11-12). Also when used, proximal section 28 is the portion of device 20 which is held by the user, and distal section 30 is the portion which cleans the tongue (refer to FIG. 12). An upwardly projecting ridge 32 is centrally disposed at proximal section 28. That is, ridge 32 runs along longitudinal centerline 34 of device 20 (refer to FIG. 4). Ridge has a first downwardly sloping side 36 which is shaped and dimensioned to receive one of the two fingers 600, and a second downwardly sloping side 38 opposite first downwardly sloping side 36 which is shaped and dimensioned to receive the other of the two fingers 600. Bottom surface 26 forms a cavity 40 at proximal end 28, cavity 40 is shaped and dimensioned to receive the thumb 700 (refer to FIGS. 8 and 10). Since body 22 is a thin member, cavity 40 is simply the opposite of ridge 32. In a broader sense, a first area is disposed on top surface 24 at proximal section 28, the first area is shaped and dimensioned to receive one of the two fingers 600; and, a second area is disposed on top surface 24 at proximal section 28, the second area is shaped and dimensioned to receive the other of the two fingers 600.

A tongue-cleaning pad 42 is disposed on bottom surface 26 at distal section 30 only. Pad 42 can be connected to body 22 by an adhesive. In an embodiment, pad 42 is kidney-shaped and is fabricated from a light colored absorbent material such as PBA sponge, which wipes and collects debris and other residue from the surface of tongue 500. The light color, which can be florescent, allows the user to see the residue which has been collected. In another embodiment, the surface of pad 42 is textured to provide a pleasurable experience when placed in contact the tongue 500. It is noted that all of top surface 24 of body 22 at distal section 30 is exposed, and is not covered by a pad.

Referring to FIG. 5, in another embodiment, tongue 500 has different areas which sense different tastes. That is, one area of tongue 500 senses sweet items, another area senses salty items, another area senses sour items, etc. A plurality of different tastes (T1, T2, T3, etc.) are disposed on pad 42. The tastes are physically located on pad 42 so that when pad 42 touches tongue 500, a taste on pad 42 abuts the area of the tongue which senses the corresponding taste (e.g. a sweet taste T1 on pad 42 abuts the sweet sensing area of tongue 500, a salty taste T2 on pad 42 abuts the salty sensing area of the tongue, etc.). It is noted that pad 42 is kidney-shaped and has a concave side which faces proximal section 28.

A first aperture 44 is disposed in first downwardly sloping side 36, first aperture 44 extending through body 22 from top surface 24 to bottom surface 26. A second aperture 46 is disposed in second downwardly sloping side 38, second aperture 46 extending through body 22 from top surface 24 to bottom surface 26. When two fingers 600 are placed on first 36 and second 38 downwardly sloping sides and thumb 700 is placed in cavity 40, the two fingers each touch the thumb (refer to FIGS. 8-10, and 13 and the associated discussions).

At proximal section 28, top 24 and bottom 26 surfaces are covered with a plurality of friction enhancing protuberances 48 (nubs). This texturing allows device 20 to be more securely held by the user. In the shown embodiment, protuberances 48 are shaped like truncated pyramids (refer also to FIG. 15).

It is noted that proximal section 28 is curved in a downward direction, and distal section 30 and pad 42 are curved in an upward direction. This curvature of body 22 is shown in FIGS. 17-22.

Device 20 further includes two downwardly projecting legs 50 connected to bottom surface 26 at proximal end 28. This feature allows a plurality of devices 20 to be stacked as a package for distribution and sale (refer also to FIG. 14 and the associated discussion).

FIGS. 8-10 are reduced side elevation, top plan, and bottom plan views respectively of device 20 being held by a user. Proximal section 28 is held with two fingers 600 and the thumb 700 of one hand. In the shown embodiment the right hand is used, however it may be appreciated that the left hand can also be used. First downwardly sloping side 36 of top surface 24 receives one of the fingers 600 (the index finger as shown), and second downwardly sloping side 38 receives the other of the fingers 600 (the middle finger as shown). It may be appreciated that other fingers 600 could be used, such as the middle finger and the ring fingers. Thumb 700 is received by cavity 40 of bottom surface 26. In other words, device is gripped between the two fingers 600 and thumb 700, with protuberances 48 facilitating the gripping process. It is further noted that when device 20 is used to clean the tongue the two fingers 600 and the thumb 700 point toward distal section 30 (refer also to FIGS. 11 and 12).

Figure 12:
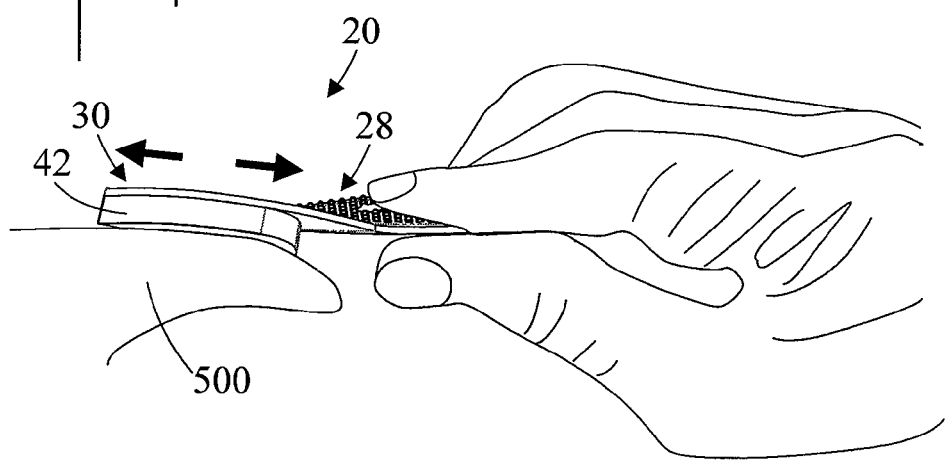
FIG. 12 is a side elevation view of the device cleaning the tongue.

FIG. 11 is a reduced side elevation view of a user preparing to use device 20, and FIG. 12 is a side elevation view of device 20 cleaning tongue 500. Pad 42 is pressed down upon tongue 500, and a longitudinal forward and back wiping action is used o clean tongue 500. The curvature of distal section 30 allows more pressure to be applied to the surface of tongue 500. The designed shape of device 20 allows it to be pressed down on tongue 500 thus allowing pressure combined with a forward and backward motion to clean, refresh and then collect debris from the surface of tongue 500. It is noted that during use pad 42 is disposed between distal section 30 and tongue 500.

Figure 13:
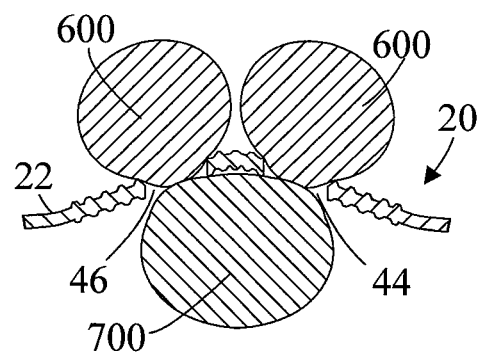
FIG. 13 is a cross sectional view along the line 13-13 of FIG. 8.

FIG. 13 is a cross sectional view along the line 13-13 of FIG. 8. First and second apertures 44 and 46 are large enough to allow fingers 600 to touch thumb 700 when device 20 is gripped. Test have shown that when the fingers 600 and thumb 700 touch, the tendency of device 20 to cause a gag reflex during use is greatly reduced.

Figure 14:
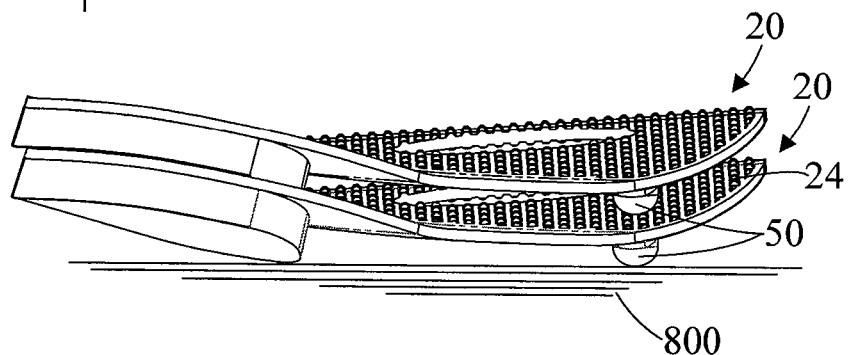
FIG. 14 is a side elevation view of two stacked devices.

FIG. 14 is a side elevation view of two stacked devices 20. It is noted that when stacked on a horizontal support surface 800, devices 20 reside in parallel spaced apart relationship. This parallel arrangement is made possible by legs 50, wherein legs 50 of an upper device 20 abut top surface 24 of a lower device 20. This feature is useful for packaging and shipping purposes. For example if device 20 is sold in packs of five, then the devices 20 will form a rectangular rather than curved stack.

Figure 15:
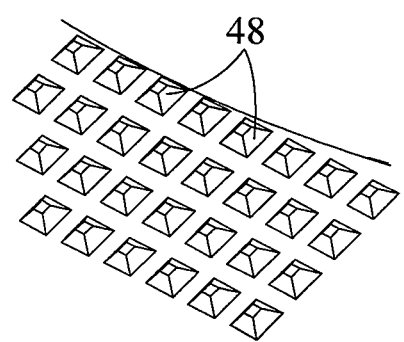
FIG. 15 is an enlarged view of area 15 of FIG. 1.

FIG. 15 is an enlarged view of area 15 of FIG. 1, showing protuberances 48. In the shown embodiment, protuberances 48 are shaped like truncated pyramids.

FIG. 16 is a top plan view of device 20 and cross sectional lines, and FIGS. 17-20 show four different cross sectional views of device 20. FIG. 17 shows the upward curvature of body 22 at distal section 30, and FIGS. 18-20 show the downward curvature of body 22 at proximal section 28.

Figure 21:
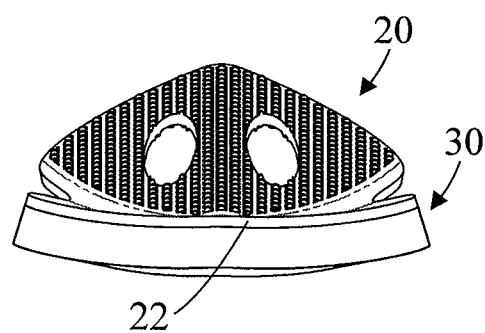
FIG. 21 is a view in direction 21 of FIG. 3.
Figure 22:
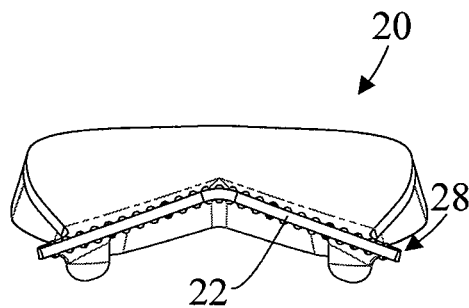
FIG. 22 is a view in direction 22 of FIG. 3.

FIG. 21 is a view in direction 21 of FIG. 3 which shows the upward curvature of body 22 at distal section 30, and FIG. 22 is a view in direction 22 of FIG. 3 which shows the downward curvature of body 22 at proximal section 28.

In an embodiment, body 22 is a thin ridged or semi-ridged member made of an inexpensive material such as cardboard or a polymer.

In terms of use, a method for cleaning a tongue 500 using two fingers 600 and the thumb 700 of one hand includes (refer to FIGS. 1-22)

(a) providing a device 20 for cleaning a tongue 500, device 20 holdable by the two fingers 600 and the thumb 700, device 20 including:

a body 22 having a top surface 24, an opposite bottom surface 26, a proximal section 28, and a distal section 30;

an upwardly projecting ridge 32 is centrally disposed at proximal section 32;

ridge 32 having a first downwardly sloping side 36 which is shaped and dimensioned to receive one of the two fingers 600;

ridge 32 having a second downwardly sloping side 38 opposite first downwardly sloping side 36, second downwardly sloping side 38 shaped and dimensioned to receive the other of the two fingers 600;

bottom surface 26 forming a cavity 40 at proximal section 30, cavity 40 shaped and dimensioned to receive the thumb 700;

a tongue-cleaning pad 42 is disposed on bottom surface 26 at distal section 28;

(b) placing one finger 600 on first downwardly sloping side 36, placing the other finger 600 on second downwardly sloping side 38, placing the thumb 700 in cavity 40, and gripping proximal section 28 between the two fingers 600 and the thumb 700; and, (c) pressing pad 42 down upon the tongue 20 and using a longitudinal forward and back wiping action to clean the tongue 500.

The method further including:

in (a), a first aperture 44 is disposed in first downwardly sloping side 36, first aperture extending through body 22 from top surface 24 to bottom surface 26;

in (a), a second aperture is 46 disposed in second downwardly sloping side 38, second aperture 46 extending through body 22 from top surface 24 to bottom surface 26; and, in (b), the two fingers 600 each touch the thumb 700.

The method further including:

in (a), two downwardly projecting legs 50 connected to bottom surface 26 at proximal section 28; and, in (a), providing a plurality of devices 20, wherein devices 20 are stacked so that legs 50 of an upper device 20 rest upon top surface 24 of a lower device 20.

The method further including:

in (a), proximal section 28 being curved in a downward direction, and distal section 30 and pad 42 being curved in an upward direction; and, in (c) upwardly curved pad 42 contacting the tongue 500.

Tongue 500 has different areas which sense different tastes, the method further including:

in (a), a plurality of different tastes (T1, T2, T3, etc.) disposed on pad 52, the tastes physically located on pad 52 so that when pad 52 touches tongue 500, a taste on pad 52 abuts the area of the tongue which senses the taste; and, in (c), positioning pad 52 so that when pad 52 touches tongue 500, a taste on pad 52 abuts the area of the tongue which senses the taste.

The embodiments of the device and method of use described herein are exemplary and numerous modifications, combinations, variations, and rearrangements can be readily envisioned to achieve an equivalent result, all of which are intended to be embraced within the scope of the appended claims. Further, nothing in the above-provided discussions of the device and method should be construed as limiting the invention to a particular embodiment or combination of embodiments. The scope of the invention is defined by the appended claims.

I claim:

1. A method for cleaning a tongue using two fingers and the thumb of one hand, comprising:

(a) providing a device for cleaning a tongue, the device holdable by the two fingers and the thumb, the device including:

a body having a top surface, an opposite bottom surface, a proximal section, and a distal section;

an upwardly projecting ridge centrally disposed at said proximal section;

said ridge having a first downwardly sloping side which is shaped and dimensioned to receive one of the two fingers;

said ridge having a second downwardly sloping side opposite said first downwardly sloping side, said second downwardly sloping side shaped and dimensioned to receive the other of the two fingers;

said bottom surface forming a cavity at said proximal end, said cavity shaped and dimensioned to receive the thumb;

a pad disposed on said bottom surface at said distal section;

two downwardly projecting legs connected to said bottom surface at said proximal section; and, providing a plurality of said devices, wherein said devices are stacked to that said legs of an upper device rest upon said top surface of a lower device (b) placing one finger on said first downwardly sloping side, placing the other finger on said second downwardly sloping side, placing the thumb in said cavity, and gripping said proximal section between the two fingers and the thumb; and, (c) pressing said pad down upon the tongue and using a longitudinal forward and back wiping action to clean the tongue.

2. The method of claim 1, further including:

in (a), a first aperture disposed in said first downwardly sloping side, said first aperture extending through said body from said top surface to said bottom surface;

in (a), a second aperture disposed in said second downwardly sloping side, said second aperture extending through said body from said top surface to said bottom surface; and, in (b), the two fingers each touch the thumb.

3. The method of claim 1, further including:

in (a), said proximal section being curved in a downward direction, and said distal section and said pad being curved in an upward direction; and, in (c) said upwardly curved pad contacting the tongue.

4. The method of claim 1, the tongue having different areas which sense different tastes, the method further including:

in (a), a plurality of different tastes disposed on said pad, said tastes physically located on said pad so that when said pad touches the tongue, a said taste on said pad abuts the area of the tongue which senses the taste; and, in (c), positioning said pad so that when said pad touches the tongue, a said taste on said pad abuts the area of the tongue which senses the taste.

5. A device for cleaning a tongue, the device holdable by two fingers and a thumb of one hand, the device comprising:
a body having a top surface, an opposite bottom surface, a proximal section, and a distal section;
said proximal section having a first downwardly sloping side which is shaped and dimensioned to receive one of the two fingers,
said proximal section having a second downwardly sloping side opposite said first downwardly sloping side, said second downwardly sloping side shaped and dimensioned to receive the other of the two fingers;
said bottom surface forming a cavity at said proximal section, said cavity shaped and dimensioned to receive the thumb;
a pad disposed on said bottom surface at said distal section only;
a first aperture disposed in said first downwardly sloping side, said first aperture extending through said body from said top surface to said bottom surface;
a second aperture disposed in said second downwardly sloping side, said second aperture extending through said body from said top surface to said bottom surface;
two downwardly projecting legs connected to said bottom surface at said proximal section, so that a plurality of said devices are stackable in parallel spaced apart relationship and,
during use one of the two fingers is positionable on said first downwardly sloping side, the other of the two fingers is positionable on said second downwardly sloping side, and the thumb is positionable in said cavity, so that the two fingers each touch the thumb.

6. The device according to claim 5, further including:
during use said pad disposed between said distal section and the tongue.

7. The device according to claim 5, further including:
all of said top surface of said body at said distal section being exposed.

8. The device according to claim 5, further including:
said pad being kidney-shaped and having a concave side which faces said proximal section.

9. The device according to claim 5, further including:
said proximal section being curved in a downward direction, and said distal section and said pad being curved in an upward direction.

10. The device according to claim 5, further including:
at said proximal section, said top and bottom surfaces covered with a plurality of friction enhancing protuberances.

11. A device for cleaning a tongue, the device holdable by two fingers and a thumb of one hand, the device comprising:
a body having a top surface, an opposite bottom surface, a proximal section, and a distal section, said proximal section being curved in a downward direction;
a first area disposed on said top surface at said proximal section, said first area shaped and dimensioned to receive one of the two fingers;
a second area disposed on said top surface at said proximal section, said second area shaped and dimensioned to receive the other of the two fingers;
a third area disposed on said bottom surface at said proximal section, said third area shaped and dimensioned to receive the thumb, so that during use the two fingers and the thumb are positionable such that they point toward said distal section;
a pad disposed on said bottom surface at said distal section only; and, two downwardly projecting legs connected to said bottom surface at said proximal section, so that a plurality of said devices are stackable in parallel spaced apart relationship.

12. The device according to claim 11, further including:
all of said top surface of said body at said distal section being exposed.

13. The device according to claim 11 further including:
said pad being kidney-shaped and having a concave side which faces said proximal section.

14. The device according to claim 11, further including:
said distal section and said pad being curved in an upward direction.

15. The device according to claim 11, further including:
at said proximal section, said top and bottom surfaces covered with a plurality of friction enhancing protuberances.

16. A device for cleaning a tongue, the device holdable by two fingers and a thumb of one hand, the device comprising:
a body having a top surface, an opposite bottom surface, a proximal section, and a distal section, said proximal section being curved in a downward direction;
said top surface at said proximal section shaped and dimensioned to receive the two fingers;
said bottom surface at said proximal section shaped and dimensioned to receive the thumb;
a pad disposed on said bottom surface at said distal section only;
all of said top surface of said body at said distal section being exposed; and, two downwardly projecting legs connected to said bottom surface at said proximal section, so that a plurality of said devices are stackable in parallel spaced apart relationship.

17. The device according to claim 16, further including:
during use said pad disposed between said distal section and the tongue.

18. The device according to claim 16, further including:
said pad being kidney-shaped and having a concave side which faces said proximal section.

19. The device according to claim 16, further including:
said distal section and said pad being curved in an upward direction.

20. The device according to claim 16, further including:
at said proximal section, said top and bottom surfaces covered with a plurality of friction enhancing protuberances.

* * * * *